United States Patent [19]

Hamada et al.

[11] Patent Number: 4,584,410

[45] Date of Patent: Apr. 22, 1986

[54] PROCESS FOR THE PREPARATION OF HYDROXYBENZALDEHYDES

[75] Inventors: Kazuhiko Hamada; Gohfu Suzukamo, both of Osaka; Fujio Masuko, Oita; Makoto Nakamura, Osaka, all of Japan

[73] Assignee: Sumitomo Chemical Co., Ltd., Osaka, Japan

[21] Appl. No.: 670,847

[22] Filed: Nov. 13, 1984

Related U.S. Application Data

[63] Continuation of Ser. No. 415,293, Sep. 7, 1982, abandoned.

[30] Foreign Application Priority Data

Sep. 7, 1981 [JP] Japan .................................. 56-141484

[51] Int. Cl.$^4$ .............................................. C07C 45/45
[52] U.S. Cl. .................................... 568/436; 568/437
[58] Field of Search ................................ 568/436, 437

[56] References Cited

PUBLICATIONS

Brady et al., Jour. Chem. Soc. (London) (1950), 767-777.
Wynberg, Chemical Reviews (1960), vol. 60, 169-170.
Hiyama et al., Tetrahedron (1974), vol. 30, 2661, 2664-2668.
Merck Index (1983), 10th Ed., 1981.

*Primary Examiner*—Bernard Helfin
*Attorney, Agent, or Firm*—Sughrue, Mion, Zinn, Macpeak & Seas

[57] ABSTRACT

In a Reimer-Tiemann reaction for the preparation of a mixture of two hydroxybenzaldehydes (i.e., salicylaldehyde and p-hydroxybenzaldehyde) by reacting phenol with chloroform and an aqueous alkali solution in a heterogeneous system, the two hydroxybenzaldehydes can be prepared in a controlled formation ratio, yield and reaction rate depending upon the conditions used when the reaction is carried out in the presence of a phase transfer catalyst selected from the group consisting of a cationic type phase transfer catalyst, an amphoteric type phase transfer catalyst and an anionic type phase transfer catalyst.

6 Claims, No Drawings

PROCESS FOR THE PREPARATION OF HYDROXYBENZALDEHYDES

This is a continuation of application Ser. No. 415,293 filed Sept. 7, 1982 and now abandoned.

FIELD OF THE INVENTION

The present invention relates to an improvement of a so-called Reimer-Tiemann reaction, i.e., a reaction of phenol with chloroform and an aqueous alkali solution in a heterogeneous system to prepare a mixture of salicylaldehyde and p-hydroxybenzaldehyde. More particularly, it relates to a process for the preparation of hydroxybenzaldehydes by the Reimer-Tiemann reaction comprising using a phase transfer catalyst in a new reaction system to thereby control the formation ratio, yield, reaction rate and the like of the mixture of salicylaldehyde and p-hydroxybenzaldehyde.

BACKGROUND OF THE INVENTION

Of the hydroxybenzaldehydes obtained by the process of the present invention, salicylaldehyde and p-hydroxybenzaldehyde are both an industrially important compound, the former being useful as an intermediate for perfumes, agricultural chemicals and chelating agents, and the latter as an intermediate for the preparation of agricultural chemicals and medicines (penicillin modifiers, etc.).

The following methods are, for example, so far known as the preparation of hydroxybenzaldehydes:

(1) So-called Conventional Reimer-Tiemann Reaction:

In accordance with this reaction, a phenol is reacted with chloroform and an aqueous alkali solution in a heterogeneous system to prepare a mixture of salicylaldehyde and p-hydroxybenzaldehyde. However, in this method, the yield of salicylaldehyde is generally low. Further, an excess amount of chloroform over the phenol is necessary, and the recovery and recycling of unreacted chloroform and phenol are difficult.

As one of typical examples of improved Reimer-Tiemann reaction method, a method wherein aqueous methanol containing 10 to 75% by weight of methanol is employed as a reaction medium is known (as disclosed in U.S. Pat. No. 3,365,500). Although this method has an advantage that the amount of formed tar (high-boiling substance) is reduced, it has so defects that the conversion of phenol is low, the separation and recovery of unreacted phenol are difficult, and the formation ratio of salicylaldehyde to p-hydroxybenzaldehyde is lower than that obtained under the ordinary Reimer-Tiemann condition. Therefore, this method accompanies difficulties in the separation of the components from the reaction mixture and the like.

(2) Method prepared by Yoel Sasson et al [*Tetrahedron Lett.*, 3753 (1979) and 1875 (1980)]:

In accordance with this method, when an aliphatic tertiary amine is added to the reaction mixture obtained under the ordinary Reimer-Tiemann condition (where excess amounts of chloroform and an aqueous alkali solution are used over the phenol), the yield of salicylaldehyde is improved without any undesirable influence over the yield of p-hydroxybenzaldehyde. But this method accompanies not a few disadvantages. Namely, the tertiary amine which can be used is limited to a few species such as $(n-C_4H_9)_3N$, etc., and a reaction to form an alkyl ether of phenol also takes place competitively. Further, excess amounts of chloroform and an aqueous alkali solution over the phenol need be used, which leads to the foregoing disadvantages. Still further, it has been experimentally confirmed by the present inventors under the same conditions as reported that the effects brought by the addition of the aliphatic tertiary amine are not so drastic as reported.

(3) A method in which salicylaldehyde is prepared in good yield by one step reaction using as starting materials a phenol and formaldehyde and a specific catalyst (a base represented by a tertiary amine and/or an organometallic salt):

This method is described in, for example, Japanese Patent Application (OPI) Nos. 34737/78 and 163538/79 (the term "OPI" as used herein refers to a "published unexamined Japanese patent application") and *J.C.S.*, Perkin I, 1862 (1980) and the like. This method, however, accompanies not a few disadvantages. In other words, an excess amount of formaldehyde over the phenol, a poisonous catalyst (e.g., $SnCl_2$, $SnCl_4$, $Cr(acac)_3$, etc.) or a fairly large amount of an organic amine as an additive need be used; and therefore, a complicated post-treatment and waste water treatment and the like are inevitable.

(4) A method for selectively obtaining p-hydroxybenzaldehyde by oxidizing p-cresol derivatives with oxygen:

This method includes, for example, a method for using an excessive amount of potassium tertiary butoxide in dimethylformamide (as described in *Angew. Chem.*, 86, 386 (1975)). In these methods, however, it is general that large amounts of a special solvent and base should be used, and that the yield of desired product is very low when substrates other than 2,6-disubstituted p-cresol are used.

SUMMARY OF THE INVENTION

In order to solve the drawbacks of the prior art methods, the present inventors have intensively studied to provide a new method for controlling the formation ratio, yield, reaction rate and the like of two hydroxybenzaldehydes (i.e., salicylaldehyde and p-hydroxybenzaldehyde) depending upon conditions employed, which leads to the finding that when if desired an organic solvent which is inert to the reaction is used, and a phase transfer catalyst is used, the recovery percentage of unreacted phenol, the reaction rate, the formation ratio and yield of salicylaldehyde/p-hydroxybenzaldehyde and the like can be controlled and improved depending upon the kind of the phase transfer catalyst, the kind and concentration of the aqueous alkali solution, the kind of the organic solvent, the ratio of the reaction reagents employed and the like.

Furthermore, the following confirmation was conducted in the course of the preparation of salicylaldehyde as a main product in the ordinary Reimer-Tiemann reaction: Confirmation of an optimum ratio of reaction reagents (phenol/chloroform/aqueous alkali solution), a method for the recovery of unreacted materials from the reaction mixture after the reaction, and a method for the separation and purification of the products; and identification of impurities and high-boiling substances produced as byproducts.

A primary object of the present invention is, therefore, to eliminate the above-described drawbacks of the prior art methods and to provide a new process for the controlled preparation of hydroxybenzaldehydes.

Another object of the present invention is to provide an improved process for the preparation of two hydroxybenzaldehydes (i.e., salicylaldehyde and p-hydroxybenzaldehyde) in a controlled formation ratio, yield, reaction rate and the like depending upon the conditions.

A further object of the present invention is to provide an improved process for reacting phenol with chloroform and an aqueous alkali solution in a heterogeneous system using a phase transfer catalyst, whereby two hydroxybenzaldehydes (i.e., salicylaldehyde and p-hydroxybenzaldehyde) can be prepared in a controlled formation ratio, yield, reaction rate and the like depending upon the conditions.

These and other objects and advantages of the present invention will be apparent to one skilled in the art from the following description.

DETAILED DESCRIPTION OF THE INVENTION

As the phenol, chloroform and alkali metal hydroxide used as reagents in the process of the present invention, those commercially available can be used as they are.

Examples of the alkali metal hydroxide which can be used include lithium hydroxide, sodium hydroxide, potassium hydroxide and cesium hydroxide, with the sodium hydroxide and potassium hydroxide being preferable because these are inexpensive. The concentration of the aqueous solution of alkali metal hydroxide which can be used is generally about 10 to about 60%. In general, the amount of salicylaldehyde formed increases whereas the amount of p-hydroxybenzaldehyde formed decreases, as the concentration of alkali metal hydroxide in the aqueous solution increases.

The formation ratio of the two hydroxybenzaldehydes (i.e., salicylaldehyde and p-hydroxybenzaldehyde) varies depending upon the kind of alkali metal hydroxide used. For example, when a 50% aqueous solution of a hydroxide is used, the formation ratio of salicylaldehyde/p-hydroxybenzaldehyde increases respectively when using the following specific compounds: lithium hydroxide, sodium hydroxide, potassium hydroxide and cesium hydroxide. In other words, the formation ratio is highest when using lithium hydroxide, somewhat lower when using sodium hydroxide, still lower when using potassium hydroxide, and lowest when using cesium hydroxide.

Examples of the organic solvent inert to the reaction which can be used as an optional component in the present invention include aromatic and aromatic halogenated hydrocarbons such as benzene, toluene, xylene and chlorobenzene; ethers such as anisole, diisopropyl ether, dibutyl ether and tetrahydrofuran; aliphatic alcohols such as methanol, ethanol and butanol; esters such as ethyl acetate and methyl acetate; ketones such as methyl isobutyl ketone; aliphatic hydrocarbons such as n-hexane and cyclohexane; heterogeneous polar solvents such as acetonitrile, dimethyl sulfoxide and dimethylformamide; and the like.

Of these solvents, in solvents forming a heterogeneous reaction system such as aromatic hydrocarbons, aliphatic hydrocarbons and ethers, not only the recovery percentage of phenol is good but also the yield of hydroxybenzaldehydes is high. On the other hand, in solvents forming a homogeneous reaction system such as polar solvents and cyclic ethers, the recovery percentage of phenol is somewhat inferior to the above. Of the solvents used in the reaction of the present invention, systems affording the best result (i.e., a yield per phenol consumed) are those aliphatic ether solvents such as dibutyl ether, diisopropyl ether and the like. The amount of the inert organic solvent used is 0.5 to 10 parts by weight, preferably 1 to 5 parts by weight, based on the phenol fed as the starting material.

Examples of the phase transfer catalyst which can be used in the reaction of the present invention include cationic type (quaternary salt type), amphoteric type and anionic type. Of these, those which are used effectively are cationic and amphoteric types. Suitable examples of the cationic type phase transfer catalyst include quaternary ammonium salts and quaternary phosphonium salts such as cetyltrimethylammonium chloride, cetyltributylphosphonium bromide, triethylbenzylammonium chloride and tetrabutylammonium hydroxide, and pyridinium salts. Of these, those which are particularly preferably used for the preparation of salicylaldehyde are cationic type quaternary salts in which the anionic moiety thereof consists of a hydroxyl group. Suitable examples of the amphoteric type phase transfer catalyst include those of betaine type and amino acid type, and those which are particularly preferably used for the preparation of p-hydroxybenzaldehyde are betaine type amphoteric agents such as lauryl betaine. Suitable examples of the anionic type phase transfer catalyst include alkali metal salts of higher fatty acid, higher alkylsulfonates, salts of sulfuric acid ester of higher alcohol and the like.

Of these, the cationic type phase transfer catalyst acts as follows: When it is used in an alkali solution having a high concentration, e.g., 40 to 60%, the recovery percentage of unreacted phenol generally increases (e.g., 89 to 95%), and at the same time, with an increase in the concentration of alkali metal hydroxide in the aqueous solution (e.g., from 10% to about 60%), the amount of, mainly, salicylaldehyde of hydroxybenzaldehydes increases. Further, it is observed that the reaction rate also increases, and generally, it amounts to 1.5 to 4 times as high as that in the case of using no catalyst. Also, when the amphoteric type phase transfer catalyst is used in an aqueous solution system having a low concentration, the amount of p-hydroxybenzaldehyde increases. A catalytic amount per the chloroform used of the phase transfer catalyst is used. For example, it is 0.1 to 20 mole%, preferably 0.5 to 5 mole%, based on the chloroform.

With respect to the feeding ratio of reaction reagents, there can be employed various conditions ranging from normal experimental conditions in which the aqueous alkali solution and chloroform are used in large excessive amounts to the phenol (for example, phenol/alkali/chloroform = 1.0/10.0/10.0, etc.) to conditions in which the alkali and chloroform are used in amounts below the assumed theoretical ones (i.e., phenol/alkali/chloroform = 1.0/4.0/1.0). The feeding ratio of a phenol/alkali/chloroform are thus exemplified to be from 1.0/10.0/10.0 to 1.0/2.0/0.33. In this case, when the amount of chloroform is large, the amount of tar which is a high-boiling substance increases and hence, it is desirable to employ a method in which the amount of chloroform is decreased whereas the amount of alkali is somewhat increased. As the optimum feeding ratio of reaction reagents, there is given, for example, a ratio of phenol/alkali (sodium hydroxide)/chloroform of 1.5/5.4/1.0, etc.

With respect to the method for separating and purifying the reaction products, the present inventors extensively studied to improve the recovery percentage of unreacted phenol and purity of the products. As a result, it was found that high-purity hydroxybenzaldehydes (i.e., salicylaldehyde and p-hydroxybenzaldehyde) can be obtained in good efficiency, for example, by a method outlined below:

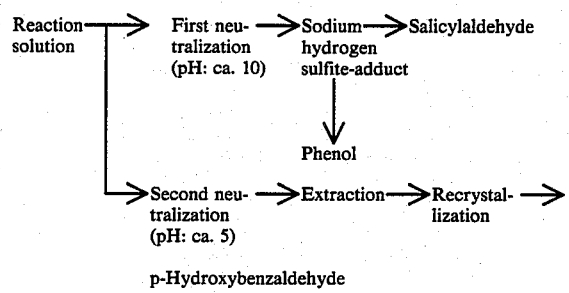

p-Hydroxybenzaldehyde

The analysis of the products of the present invention (unreacted phenol, hydroxybenzaldehydes and high-boiling substances) was principally carried out according to gas chromatographic quantitative analysis using internal standard.

Hereupon, a main component of high-boiling substances formed in small amounts by the reaction of the present invention was identified as triphenoxymethane

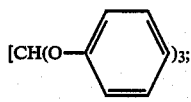

molecular weight, 292].

Further, of the two kinds of dialdehydes (1) and (2) set forth below produced in trace amounts as by-products which, however, have not so far been confirmed in the ordinary Reimer-Tiemann reaction, the present inventors were the first to identify the former (1) by isolation, gas chromatographic analysis, measurement of physical property and synthesis through another route. The latter (2) was confirmed by mass spectral analysis.

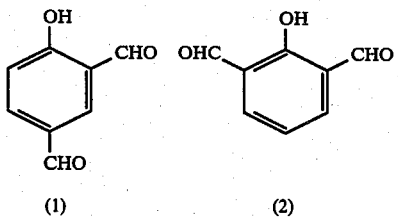

The separation and purification of these reaction products are carried out by the foregoing method to obtain two kinds of high-purity hydroxybenzaldehydes in good efficiency.

The present invention will be illustrated in more detail with reference to the following examples, which are not, however, to be interpreted as limiting the invention thereto.

EXAMPLE 1

A 50% sodium hydroxide aqueous solution comprising 86.4 g (2.16 mole) of commercially available special-grade sodium hydroxide (purity: 96.0%) and 86.4 g (4.80 mole) of water was fed into a three-necked flask equipped with a condenser, and then 56.4 g (0.6 mole) of phenol was added thereto to form a salt. Thereafter, 70 ml of di-n-butyl ether and 1.3 g of tetrabutylammonium hydroxide (40% methanol solution, 0.002 mole) were added thereto, and the resulting mixture was heated to 55° to 57° C. while slowly stirring using a stirring blade. After confirming that the temperature of the reaction system became constant and stirring can be conducted smoothly (200 to 300 rpm), 47.7 g (0.4 mole) of chloroform held in a side-tube was slowly and carefully added dropwise to the stirred solution over about 1 hour. After completion of the dropwise addition, the reaction system was kept at the same temperature with stirring for about 2.5 hours. During that period, cooling by means of a condenser required to sufficiently be carried out by using ice water in order to prevent chloroform from escaping out of the system. After completion of the temperature maintenance, the reaction system was cooled to 20° C. and hydrolyzed with a 10% hydrochloric acid aqueous solution (pH: about 5).

After separating the organic layer, the aqueous layer was extracted twice with 40 ml of ethyl acetate (or methyl isobutyl ketone). An organic layer obtained by combining these extracts and the aqueous layer were quantitatively analyzed by gas chromatography in accordance with a GC-IS method. The results obtained are shown in Table 1.

TABLE 1

| Recovery Percentage of Unreacted Phenol (%) | Product Yield per Phenol Consumed (%) | | | |
|---|---|---|---|---|
| | SAL *1 | POBA *2 | SAL + POBA | SAL/ POBA |
| 94.8 | 70.5 | 15.2 | 85.7 | 4.6 |

Note *1 Salicylaldehyde
Note *2 p-Hydroxybenzaldehyde

EXAMPLES 2 TO 19

Reaction was carried out in the same manner as in Example 1. The results obtained are shown in Table 2. SAL and POBA in the table mean the same as in Table 1.

EXAMPLES 20 TO 22

Reaction was carried out in the same manner as in Example 1. The results obtained are shown in Table 3. SAL and POBA in the table mean the same as in Table 1.

TABLE 2

| Example No. | Feeding | | | | | | Reaction Condition | | Recovery Percentage of Unreacted Phenol (%) | Product (Yield per Phenol Consumed) (%) | | | |
|---|---|---|---|---|---|---|---|---|---|---|---|---|---|
| | Phenol (mole) | Chloroform (mole) | Alkali (kind) (mole) | (aqueous solution, %) | Phase Transfer Catalyst (mole) | Inert Organic Solvent (ml) | Temperature (°C.) | Time (hr) | | SAL | POBA | SAL + POBA | SAL/POBA |
| 2 | 0.6 | 0.2 | NaOH 1.2 | (50%) | BAC*1 0.002 | n-Butyl ether 60 | 55 Chloroform added dropwise | 3.5 | 94.1 | 61.2 | 14.0 | 75.2 | 4.4 |
| 3 | 0.6 | 0.2 | NaOH 1.2 | (50%) | BAC 0.002 | Anisole 60 | 55 Same as above | 3.5 | 91.7 | 45.2 | 9.6 | 54.8 | 4.7 |
| 4 | 0.6 | 0.2 | NaOH 0.6 | (50%) | BAC 0.002 | Toluene 60 | 55 aq. NaOH and chloroform added dropwise simultaneously | 3.5 | 89.9 | 45.6 | 7.9 | 53.5 | 5.8 |
| 5 | 0.6 | 0.2 | NaOH 1.2 | (50%) | BAC 0.002 | Toluene 120 | 55 Chloroform added dropwise | 3.5 | 90.5 | 39.8 | 12.5 | 51.8 | 3.14 |
| 6 (Comparative Example) | 0.6 | 0.2 | NaOH 1.2 | (50%) | None | Toluene 120 | 55 Same as above | 5.0 | 81.2 | 32.5 | 10.5 | 43.0 | 3.09 |
| 7 | 0.6 | 0.2 | NaOH 1.2 | (70%) | BAC 0.002 | None | 55 Chloroform added dropwise | 3.5 | 80.0 | 43.2 | 5.8 | 49.0 | 7.4 |
| 8 | 0.6 | 0.2 | NaOH 1.2 | (40%) | BAC 0.002 | None | 55 Same as above | 3.5 | 84.6 | 36.9 | 16.1 | 53.0 | 2.3 |
| 9 | 0.6 | 1.2 | NaOH 2.4 | (10%) | Lauryl *2 betaine 0.006 | Benzene 100 | 75 Chloroform added dropwise | 4.0 | 78.3 | 17.1 | 43.9 | 61.0 | 0.4 |
| 10 | 0.6 | 1.2 | NaOH 2.4 | (10%) | Glycine type *3 0.006 | Benzene 100 | 75 Same as above | 5.0 | 79.2 | 28.9 | 24.1 | 53.0 | 1.2 |
| 11 | 0.6 | 0.2 | NaOH 1.2 | (50%) | BAC 0.001 | None | 55 Same as above | 3.5 | 85.0 | 43.6 | 12.8 | 56.4 | 3.4 |
| 12 | 0.2 | 0.6 | NaOH 2.0 | (50%) | BAC 0.001 | None | 55 Same as above | 3.5 | 36.7 | 40.9 | 11.1 | 52.0 | 3.7 |
| 13 | 0.6 | 0.2 | NaOH 1.2 | (50%) | BAC 0.002 | n-Hexane | 55 Same as above | 3.5 | 87.7 | 44.0 | 13.2 | 57.2 | 3.3 |
| 14 | 0.6 | 0.2 | NaOH 1.2 | (50%) | (C4H9)4NOH 0.002 | Xylene 60 | Same as above | | 91.3 | 49.1 | 12.9 | 62.0 | 3.8 |
| 15 | 0.6 | 0.2 | NaOH 1.2 | (50%) | (C4H9)4NOH 0.002 | Isopropyl ether 60 | Same as above | | 92.1 | 51.2 | 12.0 | 63.2 | 4.3 |
| 16 | 0.6 | 0.2 | NaOH 1.2 | (50%) | C12H25C6H4SO3Na 0.002 | Methanol 30 | 55 Chloroform added dropwise | 3.5 | 84.0 | 34.3 | 14.8 | 49.1 | 2.3 |
| 17 | 0.6 | 0.2 | NaOH 1.2 | (50%) | C16H33N(CH3)3Cl 0.002 | Acetonitrile 30 | Same as above | | 87.5 | 34.7 | 25.0 | 59.7 | 1.4 |
| 18 | 0.6 | 0.4 | NaOH 2.16 | (50%) | C12H25N(CH3)3Cl 0.002 | n-Butyl ether 70 | Same as above | | 93.5 | 63.7 | 13.9 | 77.6 | 4.6 |

TABLE 2-continued

| Example No. | Feeding | | | | | | Reaction Condition | | Recovery Percentage of Unreacted Phenol (%) | Product (Yield per Phenol Consumed) (%) | | | |
|---|---|---|---|---|---|---|---|---|---|---|---|---|---|
| | Phenol (mole) | Chloroform (mole) | Alkali (kind) (mole) | (aqueous solution, %) | Phase Transfer Catalyst (mole) | Inert Organic Solvent (ml) | Temperature (°C) | Time (hr) | | SAL | POBA | SAL + POBA | SAL/POBA |
| 19 | 0.6 | 0.4 | NaOH 2.16 | (50%) | [(CH$_3$)$_3$NCH$_2$C$_6$H$_5$]OH 0.002 | Isopropyl ether 70 | Same as above | | 91.1 | 53.7 | 13.1 | 66.8 | 4.1 |

Note
*1 (C$_2$H$_5$)$_3$C$_6$H$_5$CH$_2$NCl
*2 CH$_3$(CH$_2$)$_{11}$N$^{\oplus}$(CH$_3$)$_2$CH$_2$COO$^{\ominus}$
*3 (C$_{18}$H$_{17}$)$_2$NCH$_2$CO$_2$H

TABLE 3

| Example No. | Phenol (mole) | Chloroform (mole) | Alkali (kind) (mole) | Alkali (aqueous solution, %) | Phase Transfer Catalyst (mole) | Inert Organic Solvent (ml) |
|---|---|---|---|---|---|---|
| 20 | 0.6 | 0.2 | KOH 1.2 | (50%) | $(C_4H_9)_4NOH$ 0.003 | n-Butyl ether 60 |
| 21 | 0.6 | 0.2 | KOH 1.2 | (50%) | $(C_4H_9)_4NOH$ 0.003 | Benzene 60 |
| 22 | 0.6 | 0.2 | LiOH 1.2 | (50%) | $[(CH_3)_3NCH_2C_6H_5]OH$ 0.003 | Anisole 60 |

| Example No. | Reaction Condition Temperature (°C.) | Reaction Condition Time (hr) | Recovery Percentage of Unreacted Phenol (%) | Product (Yield per Phenol Consumed) (%) SAL | POBA | SAL + POBA | SAL/POBA |
|---|---|---|---|---|---|---|---|
| 20 | 60 Chloroform added dropwise | 4.5 | 90.2 | 37.7 | 23.6 | 61.3 | 1.6 |
| 21 | Same as above | | 91.3 | 28.0 | 21.5 | 49.5 | 1.3 |
| 22 | 60 Chloroform added dropwise | 5.0 | 88.0 | 43.3 | 7.3 | 50.6 | 5.9 |

While the invention has been described in detail and with reference to specific embodiments thereof, it will be apparent to one skilled in the art that various changes and modifications can be made therein without departing from the spirit and scope thereof.

What is claimed is:

1. A process for the preparation of a mixture of salicylaldehyde and p-hydroxybenzaldehyde by the reaction of phenol with chloroform and an aqueous alkali solution in a heterogeneous system wherein the improvement comprises carrying out the reaction in the presence of a phase transfer catalyst selected from the group consisting of a cationic type quaternary salt and an amphoteric type phase transfer catalyst and in the presence of one or more aliphatic non-cyclic ether solvents.

2. A process of claim 1, wherein said cationic type quaternary salt is selected from the group consisting of a quaternary ammonium salt type phase transfer catalyst and a pyridinium salt type phase transfer catalyst.

3. A process of claim 2, where said quaternary ammonium salt type phase transfer catalyst is selected from the group consisting of trimethylbenzylammonium hydroxide and tetrabutylammonium hydroxide.

4. A process of claim 1, wherein said amphoteric type phase transfer catalyst is a betaine type phase transfer catalyst or an amino acid type phase transfer catalyst.

5. A process of claim 4, wherein said amphoteric type phase transfer catalyst is a betaine type phase transfer catalyst.

6. A process of claim 1, wherein said phase transfer catalyst is used in an amount of 0.1 to 20 mol% based on mol of the chloroform.

* * * * *